(12) United States Patent
Tsukamoto

(10) Patent No.: US 8,003,762 B2
(45) Date of Patent: *Aug. 23, 2011

(54) MONOCLONAL ANTIBODY TO CD166 AND METHOD FOR PRODUCTION THEREOF

(75) Inventor: Yasuhiro Tsukamoto, Takatsuki (JP)

(73) Assignees: Japan Science and Technology Agency, Saitama (JP); Osaka Prefecture University Public Corporation, Osaka (JP)

( * ) Notice: Subject to any disclaimer, the term of this patent is extended or adjusted under 35 U.S.C. 154(b) by 201 days.

This patent is subject to a terminal disclaimer.

(21) Appl. No.: 12/085,674

(22) PCT Filed: Nov. 28, 2006

(86) PCT No.: PCT/JP2006/323662
§ 371 (c)(1),
(2), (4) Date: May 29, 2008

(87) PCT Pub. No.: WO2007/063825
PCT Pub. Date: Jun. 7, 2007

(65) Prior Publication Data
US 2009/0269787 A1  Oct. 29, 2009

(30) Foreign Application Priority Data
Nov. 29, 2005 (JP) .................... 2005-344779

(51) Int. Cl.
*C07K 16/00* (2006.01)
*C12Q 1/00* (2006.01)
*G91N 33/53* (2006.01)

(52) U.S. Cl. ........ 530/387.1; 435/4; 435/7.1; 530/388.1

(58) Field of Classification Search ........................ None
See application file for complete search history.

(56) References Cited

U.S. PATENT DOCUMENTS 5,998,172 A * 12/1999 Haynes et al. ............. 435/70.21

OTHER PUBLICATIONS

Piazza et al, J Cell Sci. vol. 118, pp. 1515-1525, Apr. 2005.*
Kempen et al , JBC 276:25783-90, 2001.*
Piazza et al, J of Cell Science, vol. 118, p. 1515-1525, published online Mar. 2005.*
Bowen et al , Eur J Immuno 27:01469-1478, 1997.*
Sequence search result (Hynes), 2010.*
Mesh word search result (CD166), 2010.*

* cited by examiner

*Primary Examiner* — Misook Yu
*Assistant Examiner* — Lei Yao
(74) *Attorney, Agent, or Firm* — Wenderoth, Lind & Ponack, LLP

(57) ABSTRACT

CD166 is a cell adhesion molecule belonging to an immunoglobulin superfamily that is expressed in an excessive amount on the tumor surface. If an monoclonal antibody specifically binding to the CD166 is obtained, it becomes possible to suppress growth of tumor cells, detect the cells, and supply a therapeutic drug thereto specifically. However, because the CD166 proteins are very similar to each other among mammals, it was not possible to obtain an antibody to human CD166, by immunizing, for example, mice with the human CD166.
The antibody was prepared by immunizing mice with a purified avian CD166 protein. The antibody was found to be adsorbed on human and mouse CD166 proteins in vitro as well as in vivo and to have an action to suppress tumor growth in mice.

5 Claims, 6 Drawing Sheets

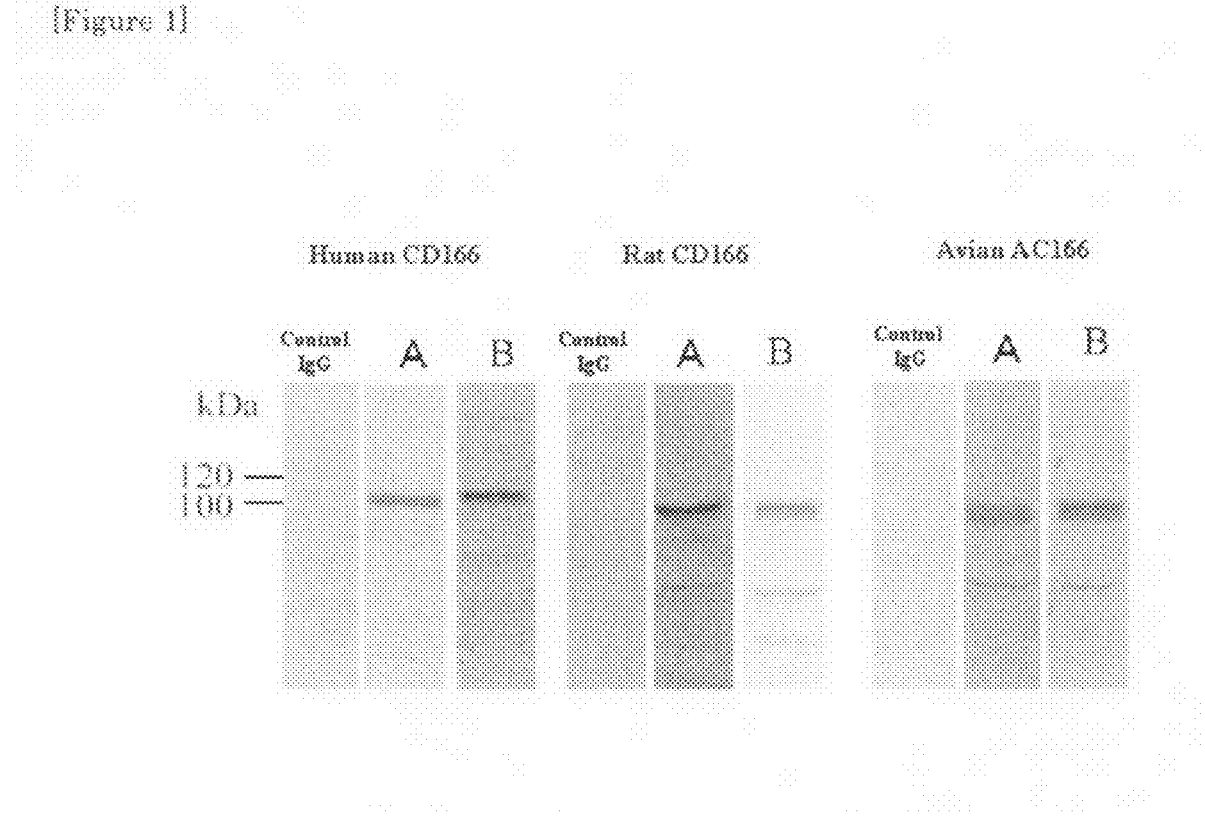
[Figure 1]

[Figure 2]
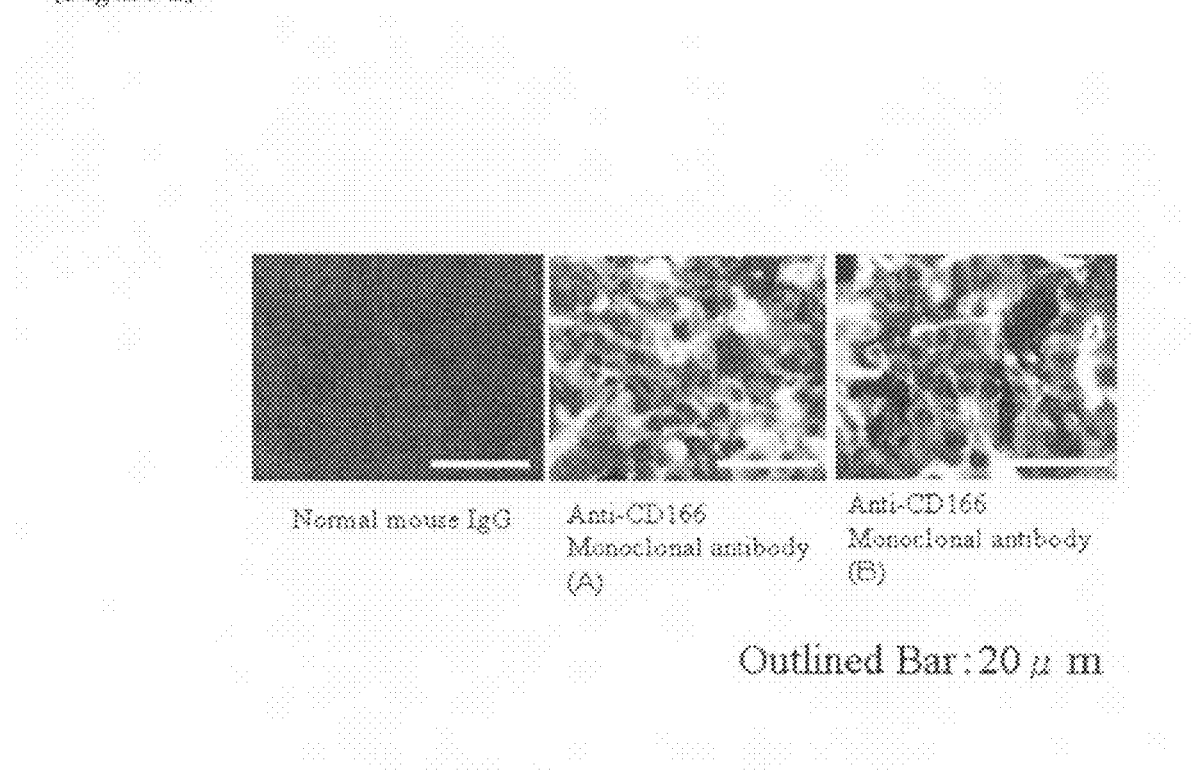
Outlined Bar: 20 μm

[Figure 3]
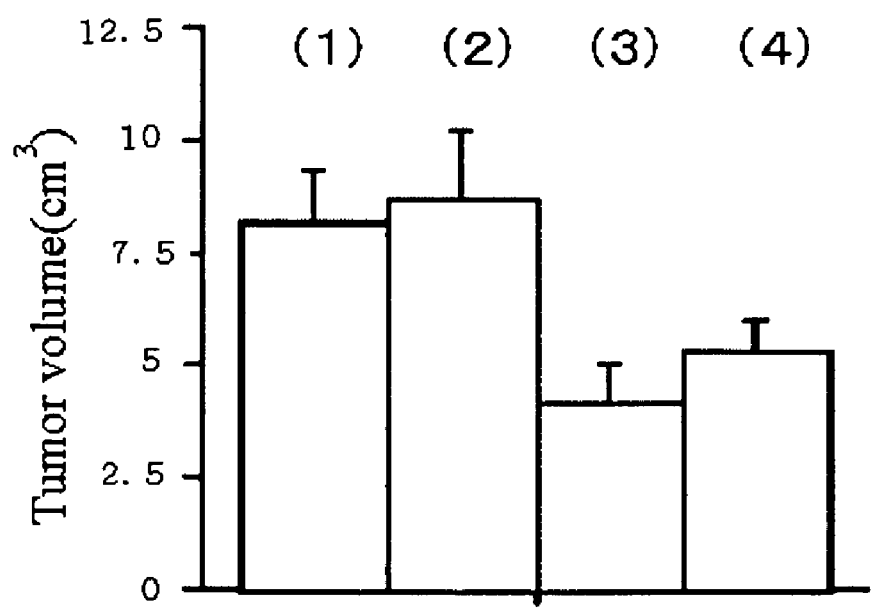

[Figure 4]
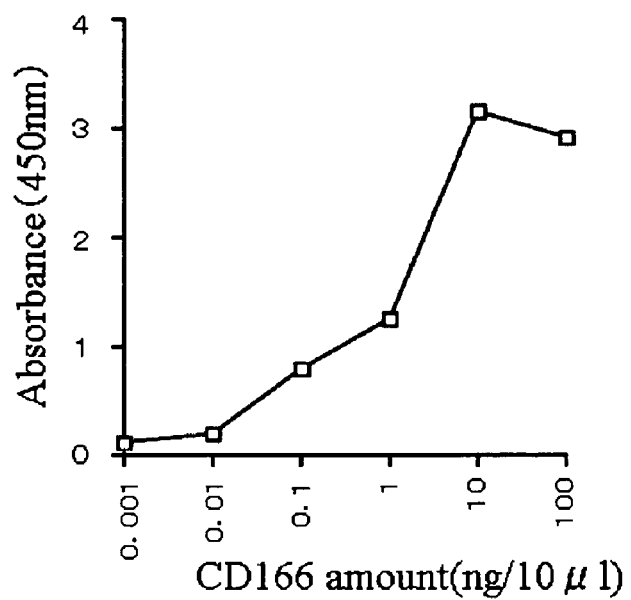
Relationship between ELIZA CD166 concentration and absorbance (450nm)

[Figure 5]
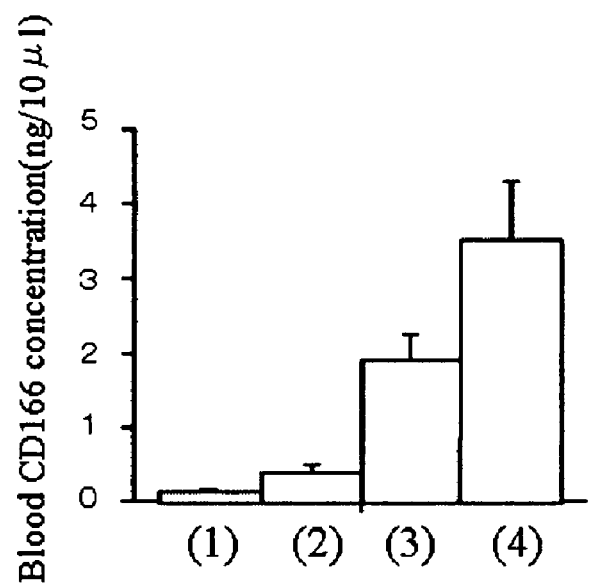
(1): Normal mouse blood serum
(2): Lung cancer-transplanted mouse blood serum (early phase)
(3): Lung cancer-transplanted mouse blood serum (intermediate phase)
(4): Lung cancer-transplanted mouse blood serum (late phase)

[Figure 6]
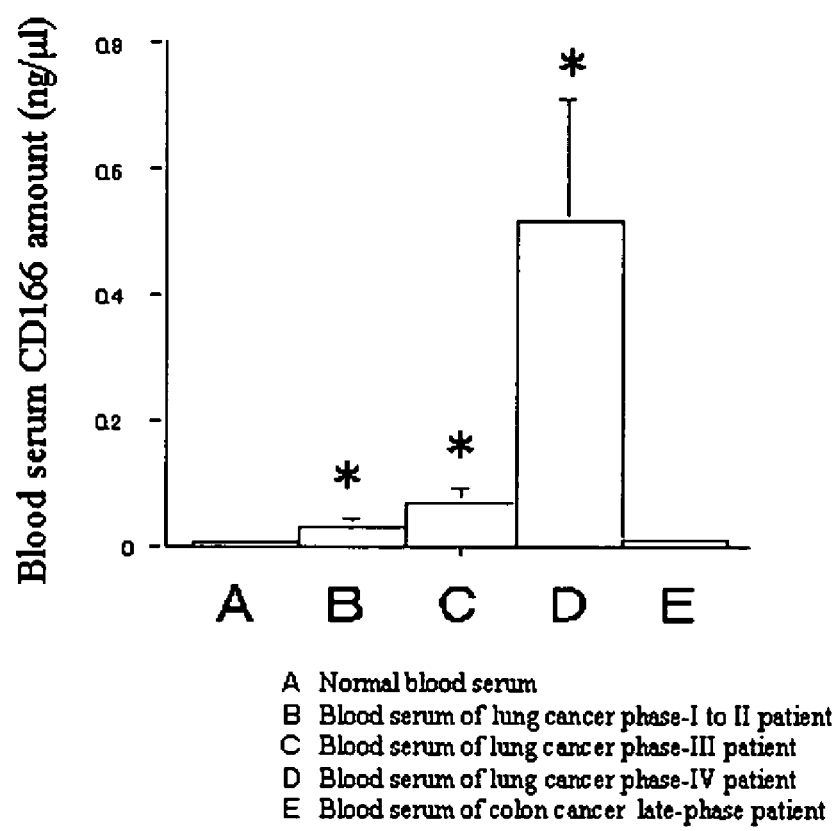

SEQUENCE LISTING

<160> NUMBER OF SEQ ID NOS: 2

<210> SEQ ID NO 1
<211> LENGTH: 22
<212> TYPE: PRT
<213> ORGANISM: mouse
<220> FEATURE:

```
-continued

<221> NAME/KEY: MISC_FEATURE
<222> LOCATION: (20)..(20)
<223> OTHER INFORMATION: Sec

<400> SEQUENCE: 1

Gln Ile Gly Glu Ala Leu Pro Val Ser Cys Thr Ile Ser Ser Ser Arg
1               5                   10                  15

Asn Ala Thr Xaa Phe Trp
            20

<210> SEQ ID NO 2
<211> LENGTH: 20
<212> TYPE: PRT
<213> ORGANISM: mouse

<400> SEQUENCE: 2

Ala Leu Pro Val Ser Cys Thr Ile Ser Ser Ser Arg Asn Ala Thr Val
1               5                   10                  15

Phe Trp Ile Lys
            20
```

MONOCLONAL ANTIBODY TO CD166 AND METHOD FOR PRODUCTION THEREOF

TECHNICAL FIELD

The present invention relates to a monoclonal antibody binding to CD166/ALCAM (Activated Leukocyte Cell Adhesion Molecule, hereinafter referred to simply as "CD166") expressed specifically in tumor cells at high frequency and a method for production thereof.

BACKGROUND ART

Antibodies for cancer treatment, which act on cancer cells, would be effective for treatment of cancers that are not easily treated with conventional anticancer agents ("sites that are not easily treated with conventional anticancer agents" or "cancers that are not easily treated with conventional anticancer agents") and in reducing the adverse effects of such therapies. Accordingly, increase in kind and improvement in quality of cancer-specific therapeutic antibodies would lead to more favorable therapeutic results in cancer therapy. For that purpose, there is a need to further study on proteins expressed specifically in cancers.

A monoclonal antibody specifically binding to human epithelial cell adhesion molecule (EpCAM), one of such proteins, was disclosed (see Patent Document 1).

EpCAM is a cell adhesion molecule expressed at a very low level on the tip of epithelial cell surface but at high rate on the epithelial tumor cell. Accordingly, EpCAM can be used as a tumor-specific marker. The monoclonal antibody, which binds to EpCAM specifically, can be used, for example, for drug delivery.

A cell adhesion molecule is a molecule governing adhesion between cells or between cell and cytoskeleton. The history goes back to 1976 A.D., when Edelman et al. studied a neural cell adhesion molecule.

In past studies, the cell adhesion molecules are divided, based on the size, into four groups: integrins, cadherins, selecting, and immunoglobulin superfamily (IgSF).

The cell adhesion molecules, which are mostly molecules expressed specifically in cancer cells, studied intensively recently. A molecule particularly attracting attention is CD166.

CD166 is a cell adhesion molecule belonging to the immunoglobulin superfamily. Such a molecule has an important role in development of nervous system and is expressed in an excess amount in particular kinds of cancer cells. In particular, the molecules are considered to accelerate malignant transformation of cancer cells and metastasis of cancers (see Nonpatent Literatures 1 to 3).

Therefore, the monoclonal antibody to CD166, if present, would be useful for prevent of metastasis and for use as a drug delivery system. Focusing on CD166, the inventors have prepared an anti-CD166 polyclonal antibody and an anti-CD166 monoclonal antibody and used them for detection of CD166 (see Patent Document 2).

Patent Document 1: Japanese Unexamined Patent Publication No. 2004-533248
Patent Document 2: Japanese Unexamined Patent Publication No. 2005-127754
Nonpatent Literature 1: J. Exp. Med., 181, 2213-2220, (1995)
Nonpatent Literature 2: Am. J. Pathol, 152, 805-813, (1998)
Nonpatent Literature 3: Biochem. Biophys. Res. Cummun., 267, 870-874 (2000)

SUMMARY OF THE INVENTION

Problems to be Solved by the Invention

Cancer cells are characteristic in that the cells remain alive without apoptosis and that the cells proliferate autonomously, independently of contact inhibition of cells. It is possible to suppress proliferation of the cancer cells, if one of the characteristics of the cells above is reduced by some means.

The characteristic that the cells proliferate over the contact inhibition was seemingly related to the adhesion molecule expressed on the surface of cancer cells. CD166 belonging to the immunoglobulin superfamily, which is expressed in cancer cell in an excessive amount, has been considered to be a protein highly related to the contact inhibition.

For that reason, if there is an antibody to be adsorbed specifically on CD166, it may be possible to detect cancer cells and deliver a drug, and thus, prevent growth of the cancer. As described in Patent Document 2 above, the inventors had succeeded in preparing a monoclonal antibody binding to the CD166 protein, but could not identify the amino acid sequence of the protein recognizing the antibody at the time. In addition, the inventors could not confirm the action of the monoclonal antibody to inhibit growth of cancer cells.

Further, there were still problems to be overcome in obtaining the CD166 antibody (monoclonal antibody), as will be described below. Normally, monoclonal antibodies are produced by administering an antigen into mice and preparing an immortalized hybridoma producing the antibodies produced in the mice.

However, because mammal CD166's are higher in homology, it is not easy to produce in mice a monoclonal antibody that is adsorbed specifically on human CD166 protein and inhibits cell adhesion action.

Thus, the anti-CD166 antibody prepared in the past as described above seemed to have an insufficient degree of specific adsorption.

Means to Solve the Problems

In the present invention, which was made to solve the problems above, a potent monoclonal antibody crossing a greater number of animal species was prepared by immunizing mice with a purified avian CD166 protein.

More specifically, CD166 has five loops of disulfide bond-containing amino acid sequence called Ig domains. An amino acid sequence including a sugar chain-binding site (amino acid sequence of NAT, i.e., of the region having asparagine, alanine and threonine), in the domains is purified artificially, and the protein is used for immunization of mice.

The purified amino acid sequence is that derived from chicken. In this way, it is possible to produce an antibody specific thereto, because the chicken protein is recognized as a foreign matter by mice. A hybridoma producing a monoclonal antibody that is adsorbed specifically on CD166 is constructed by using the antibody. Especially in the present invention, it is possible to obtain a monoclonal antibody binding to the sugar chain-binding site in the fourth immunoglobulin-like loop from the N terminal.

Advantageous Effect of the Invention

The antibody inhibited intercellular adhesion of cancer cells under culture condition and restricted motility of the cancer cells by binding to CD166 on the cancer cell membrane. When the antibody was administered into a mouse with a cancer experimentally, growth and metastasis of the cancer was restricted since then. The results suggest that the anti-CD166 monoclonal antibody according to the present invention can be used as a new therapeutic anticancer antibody.

In addition, the antibody bound to cancer cells selectively in the patient body. Thus, the antibody labelled with an anticancer agent or a radioisotope, if administered, would be delivered to the cancer-affected area efficiently and thus, the antibody may provide a new delivery system. In other words, the antibody would be effective in improving the efficiency of cancer therapy.

BRIEF DESCRIPTION OF THE DRAWINGS

FIG. 1 is a photograph showing that the antibodies A and B according to the present invention are adsorbed on CD166, as demonstrated by Western Blotting method.

FIG. 2 is a photograph showing that the antibodies A and B according to the present invention are adsorbed on tumor in vivo.

FIG. 3 is a graph showing that the antibodies A and B according to the present invention have a tumor growth-inhibiting action.

FIG. 4 is a graph showing the content of CD166, as determined by a ELISA method by using the antibody according to the present invention.

FIG. 5 is a graph showing the results of the CD166 concentration increasing along with progress of cancer, as determined by using the antibody according to the present invention.

FIG. 6 is a graph showing the results of the human CD166 concentration increasing along with progress of cancer, as determined by using the antibody according to the present invention.

DESCRIPTION OF THE PREFERRED EMBODIMENTS

The amino acid sequence and the gene sequence of CD166 are already known. For example, the amino acid and gene sequences of human CD166 are registered in databases (DDBJ/EMBK/GenBank databases) with an accession number of L38608 (and NM_001627).

As described above, avian CD166 is used in the present description. The amino acid and gene sequences of the avian CD166 are also known. The amino acid sequence of the antigen was obtained by a recombinant from the gene sequence. A "NAT" region in the amino acid sequence of avian CD166 was screened, and a sequence containing the same was chosen and identified as the amino acid sequence of the antigen.

A molecule with the desired amino acid sequence is obtained by a common recombinant method, from the gene sequence corresponding to the chosen sequence. A mouse is immunized with the molecule as an antigen for production of the antibody. Cells obtained from mouse spleen are converted to hybridoma, and the monoclonal antibody is obtained therein. A hybridoma generation method (Kohler, G. and Milstein, C., Nature 256, 495-497 (1975)) may be used for that purpose, but the hybridization method is not limited thereto.

Hereinafter, favorable examples of the present invention will be described. However, it should be understood that the present invention is not restricted by these Examples. The amino acid sequences used in the present description will be expressed as abbreviated by a common method in the art, and the examples thereof are listed below. The amino acids, if they have optical isomers, are L isomers, unless specified otherwise.

Abbreviation of Amino Acids:
Three characters: One character: Amino acid
Gly: G: glycine
Ala: A: alanine
Val: V: valine
Leu: L: leucine
Ile: I: isoleucine
Ser: S: serine
Thr: T: threonine
Cys: C: cysteine
Met: M: methionine
Glu: E: glutamic acid
Asp: D: aspartic acid
Lys: K: lysine
Arg: R: arginine
His: H: histidine
Phe: F: phenylalanine
Tyr: Y: tyrosine
Trp: W: tryptophan
Pro: P: proline
Asn: N: asparagine
Gln: Q: glutamine
Sec: U: selenocysteine

EXAMPLES

Example 1

Preparation of Monoclonal Antibody

Six-week old male BALB/c mice were immunized as an antigen with the amino acids of SEQ ID Nos. 1 and 2 in the following Table 1 constituting part of the 4th immunoglobulin-like loop from the N-terminal of an avian CD166 (alias, SC1, BEN, ALCAM) protein.

TABLE 1

| SEQ ID No. 1 | QIGEALPVSCTISSSRNATUFW |
|---|---|
| SEQ ID No. 2 | ALPVSCTISSSRNATVFWIK |

In the first immunization a mixture of 125 μg of the synthetic peptide and a complete adjuvant was administered intracutaneously. Two weeks after the first immunization a mixture of 125 μg of the synthetic peptide and an incomplete adjuvant was administered intracutaneously as the booster for a total of three times in every two weeks.

The increase of the mouse antibody titer was monitored by ELISA method. Spleen cells of the individual mouse having an increased antibody titer and myeloma cells (NS-1) were fused with each other by using polyethylene glycol (PEG), according to the method of Koehler and Milstein (Nature, 256, 495, 1975).

Subsequent hybridoma screening by a common method of using HAT (hypoxanthine, aminopterin and thymidine) and cloning by ultimate dilution method gave two kinds of antibody-producing hybridomas (A and B) recognizing the CD166 protein. Hereinafter, the antibody produced by the antibody-producing hybridoma A will be referred to as antibody A, while the antibody produced by the antibody-producing hybridoma B as antibody B.

Specifically, the antibody A is the monoclonal antibody produced in the hybridoma A of the mouse immunized with the synthetic peptide of SEQ ID No. 1, while the antibody B is the monoclonal antibody produced in the hybridoma B derived from the mouse immunized with the synthetic peptide of SEQ ID No. 2. The subclass of the antibody A was found to be IgG1, while that of the antibody B, IgG2.

The two kinds of hybridomas were planted in the abdominal cavity of a nude mouse, and the abdominal dropsy was collected, approximately 3 weeks later. The IgG's were purified from the abdominal dropsy, by a common method by using Protein A, a protein binding to IgG's specifically. Thus, it was found that two kinds of hybridomas obtained could secret the antibodies into the culture solution, be transplanted into mice and also secret the antibodies into the abdominal dropsy.

Western blot analysis showed that the monoclonal antibodies obtained recognized the CD166 proteins obtained from human lung cancer cell, rat colon cancer, and avian embryo cell membrane fraction. The results are shown in FIG. 1.

The results in FIG. 1 were obtained specifically according to the following procedure: The CD166 proteins derived respectively from human lung cancer cell (A549), rat colon cancer cell, and avian embryo cell membrane fraction were boiled in distilled water, allowing disassembly of the super molecular structures. Each of the proteins was mixed with 8% SDS (sodium dodecylsulfate), allowing adsorption of SDS.

The gel used was prepared by radical polymerization of a mixed solution of acrylamide and N,N'-methylene bisacrylamide with APS (ammonium persulfate). The polymerization initiator used was TEMED (tetramethylethylenediamine).

Each SDS-adsorbed CD166 was subjected to electrophoresis in the gel. The SDS-PAGE (SDS acrylamide gel electrophoresis) of each CD166 is complete by the procedure above.

The proteins in the gel after electrophoresis were then adsorbed on a PVDF (polyvinylidene difluoride) film. The PVDF film was then allowed to react with normal mouse IgG (immunoglobulin G) and the antibodies A and B according to the present invention.

It is then allowed to react with an anti-mouse IgG antibody labelled with HRP (peroxidase), and a photograph thereof was taken on X-ray film by ECL (enhanced chemiluminescence), giving the results shown in FIG. 1.

The anti-mouse IgG antibody is absorbed on the mouse-derived IgG specifically. The antibodies A and B obtained in the present invention, which are found to be IgG's by flow cytometry as described above, are absorbed on normal mouse IgG, the antibody A or the antibody B, if present, as a labelled antibody. The HRP label emits a light at a wavelength of 428 nm by ECL, and thus, the location is observed as a black line on X-Ray photograph. Accordingly, the region of the mouse-derived IgG if present on the PVDF film is observed as a black line.

In FIG. 1, CD166 migrated to the region of approximately 100 to 120 KDa (kilo Dalton) in size by electrophoresis. Each of the human lung cancer cell (indicated by "human CD166" in FIG. 1), the rat colon cancer cell ("rat CD166") and the avian embryo cell membrane fraction-derived CD166 ("avian CD166") formed visible black lines with the antibody A ("A") and the antibody B ("B") in the region of 100 to 120 KDa. The regions indicated by arrow in each lane of FIG. 1 correspond to the black lines formed when the antibodies A and B reacted with CD166. The results indicate that the antibodies A and B had reacted with CD166. In other words, the antibodies A and B were adsorbed on CD166.

On the other hand, normal mouse IgG ("Control IgG") gave no black line, indicating that the normal IgG was not adsorbed on CD166.

Example 2

It was shown in Example 1 that the antibodies A and B according to the present invention were adsorbed specifically on CD166 in vitro. Thus, specific adsorption in vivo was also studied.

$10^6$ pieces of human lung cancer cells (A549 cells) were inoculated in the cervical part of a nude mouse subcutaneously, and on the 21st day, 100 μg respectively of normal mouse IgG and the two kinds of anti-CD166 monoclonal antibodies (antibodies A and B) were administered from tail vein.

The tumor was removed, 12 hours after administration, and a frozen section thereof was prepared. The results after reaction with a FITC-labelled anti-mouse IgG antibody are shown in FIG. 2. The white bar in the photograph of FIG. 2 has a size of 20 micrometers. The FITC-labelled antibody if present appears white. The results show that there was almost no FITC-labelled antibody in the frozen section of normal mouse IgG.

On the other hand, the antibodies A and B was present in the while region, indicating that they were adsorbed specifically, also in vivo in the tumor region. The results indicated that the monoclonal antibody according to the present invention had a function as a DDS (Drug Delivery System).

Example 3

Antitumor Action of Anti-CD166 Monoclonal Antibody

The growth-prohibiting action of the antibodies A and B according to the present invention was then examined. $10^6$ pieces of human lung cancer cells (A549 cell) were inoculated in the cervical part of a nude mouse subcutaneously, and on the 5th, 10th, and 14th days, 100 μg respectively of normal mouse IgG and the two kinds of anti-CD166 monoclonal antibodies (antibodies A and B) were administered into the abdominal cavity.

The tumor volume of the mouse group administered with each antibody was determined, 3 weeks (21st day) after administration, and the results are shown in FIG. 3. In the Figure, the rod (1) corresponds to a case where only cancer cells were inoculated and no normal mouse IgG or the antibodies A or B was added.

The bar (2) shows the results obtained when normal mouse IgG was added, which are almost similar to those when nothing was added. On the other hand, the bars (3) and (4) show the results obtained when the antibodies A and B were added respectively, revealing distinctively a significant difference from those in the cases of (1) and (2), specifically that the antibodies A and B according to the present invention had a tumor growth-suppressing action.

The results also showed that the proliferation of the tumor cells could be restricted by making the antibodies adsorbed to the sugar chain region in the 4th immunoglobulin-like loop from the N-terminal of CD166 expressed on the surface of tumor cell.

Example 4

The Antibodies A and B According to the Present Invention are Also Applicable to ELISA (Enzyme-Linked Immunosorbent Assay)

The antibody A according to the present invention was placed on a 96-well microtiter plate (well) commonly used and left at 4° C. overnight, allowing immobilization of the antibody A on the internal surface of the well. Separately, a CD166 protein purified from human lung cancer cell A549 membrane fraction was diluted with a phosphate buffer (10 mM sodium phosphate, 150 mM NaCl, pH 7.2) to a concentration of 100 ng/10 μl, and the solution was diluted (10 times) stepwise with the phosphate buffer, to give solutions at concentrations of 0.001 to 100 ng/10 μl.

These CD166-containing solutions were placed respectively in the wells and incubated at 37° C. for 1 hour, allowing binding with the antibodies therein. Each well was washed with the phosphate buffer thrice.

A HRP-labelled anti-CD166 rabbit polyclonal antibody previously diluted 1000 times with the phosphate buffer was added to each well, and the mixture was incubated at 37° C. for 1 hour. The well was washed with the phosphate buffer thrice. In this way, sandwiched ELISA was performed.

The absorbance of the light at a wavelength of 450 nm in each well was determined by using a plate reader. A graph of the absorbance plotted against CD166 concentration is shown in FIG. 4.

In FIG. 4, the absorbance of the light at 450 nm is plotted on the ordinate, while the CD166 concentration (ng/10 μl) on the abscissa. The absorbance is a value expressed by $I_0/(I_0-I)$, i.e, the rate of the intensity of the standard light designated by $I_0$ to the value of the standard intensity $I_0$ subtracted by the intensity of the transmitted light I.

The graph confirmed that the absorbance varied according to the content of CD166. In addition, the detection range was 0.01 to 10 (ng/10 μl). The results showed that the antibody according to the present invention was applicable to CD166 measurement by ELISA. It was found that the antibody B gave similar results.

Because the antibody according to the present invention was found to be applicable to ELISA, it is possible to obtain an ELISA kit in combination of a well carrying the immobilized antibody A or B according to the present invention and a HRP-labelled anti-CD166 rabbit polyclonal antibody. It is also possible to prepare an antibody affinity column.

Example 5

Hereinafter, monitoring of progress of cancer, based on a blood test by the ELISA of Example 4 will be described. As described above, CD166 is a molecule expressed in abundance on the surface of cancer cell, but the concentration of the blood CD166 increases gradually along with progress of the cancer. It is possible to monitor progress of cancer semi-quantitatively by examining the blood concentration by ELISA.

Human lung cancer cells A549 were inoculated in the cervical part of nude mice (n: 10) subcutaneously. The blood was collected respectively from the mice on the 7th (early phase), 14th (intermediate phase, and 21 the days (terminal phase). Each of these bloods was centrifuged, to give 100 microliter of the blood sera. The CD166 content of the blood sera was determined by the ELISA method of Example 4.

Results are summarized in FIG. 5. In FIG. 5, the blood concentration (ng/10 μl) of CD166, as determined by using the relation ship between the CD166 content and the absorbance obtained in Example 4, is plotted on ordinate, and the progress of cancer on abscissa. The rod (1) of abscissa corresponds to the normal mouse blood serum; the rod (2), to the blood serum of the mice on the 7th day after transplantation of lung cancer (early phase); the rod (3), to that on the 14th day; and the rod (4), to that on the 21 the day.

ELISA by using the antibody A according to the present invention showed that the blood concentration increased along with progress of cancer. Accordingly, the monitoring method can be applicable to cancer diagnosis by using blood.

Example 6

In the present Example, progress of cancer was monitored by measuring the human blood CD166.

After informed consent by patients in the format approved by the institutional review board, Osaka Prefectural University, the following tests were preformed by using normal blood sera (A), blood sera of phase-I to II lung cancer patients (B), blood sera of phase-III lung cancer patients (C), blood sera of phase-IV lung cancer patients (D), and blood sera of terminal colon cancer patients (E).

The CD166 content in 5 μl of each of the blood sera (A to E) was determined by the ELISA method of Example 4. Results are summarized in FIG. 6. In FIG. 6, the blood CD166 concentration (ng/μg), as determined by using the relationship between the CD166 content and the absorbance obtained in Example 4, was plotted on the ordinate, while the kind of sera A to D on the abscissa.

The blood serum CD166 values of the lung cancer patients (B to E) were significantly larger than the normal CD166 value ($P<0.05$ (Student's t-test)). FIG. 6 also shows that the CD166 value was larger even in the early phase of lung cancer (B). On the other hand, there was no increase of CD166 value in the terminal colon cancer patients (E).

The present Example shows that the measurement of blood CD166 concentration is applicable as a test method of lung cancer.

INDUSTRIAL APPLICABILITY

The present invention is applicable to tumor therapy in medical institutions. It is also applicable to the tumors in depth or complicated that are not easily treated by surgical approach. It also allows reduction of adverse reactions and reduces the burden on cancer patients.

Because the cancer site can be detected by administration of an anti-CD166/ALCAM antibody, the present invention is applicable as part of medical examination for example as a PET method.

What is claimed is:

1. A monoclonal antibody, which specifically binds to the amino acid sequence of SEQ ID NO: 1 of cell adhesion molecule CD166/ALCAM.

2. The monoclonal antibody according to claim 1, wherein the subclass of the monoclonal antibody is immunoglobulin G.

3. A hybridoma, which produces the monoclonal antibody of claim 1.

4. A method of producing a monoclonal antibody, comprising purifying antibodies obtained from a mouse immunized with the amino acid sequence of SEQ ID NO: 1 to obtain a monoclonal antibody.

5. A method of measuring the level of CD166 in a sample, comprising contacting the monoclonal antibody according to claim 1 with the sample to thereby measure the level of CD166.

* * * * *